United States Patent [19]
Wheelock et al.

[11] Patent Number: 5,529,899
[45] Date of Patent: Jun. 25, 1996

[54] IMMUNOASSAY FOR AH RECEPTOR TRANSFORMED BY DIOXIN-LIKE COMPOUNDS

[75] Inventors: Geoffrey D. Wheelock, Ithaca; John G. Babish, Brooktondale, both of N.Y.

[73] Assignee: Cornell Research Foundation, Inc., Ithaca, N.Y.

[21] Appl. No.: 98,142

[22] Filed: Jul. 27, 1993

Related U.S. Application Data

[63] Continuation-in-part of Ser. No. 795,193, Nov. 19, 1991, abandoned, which is a continuation-in-part of Ser. No. 792,922, Nov. 15, 1991, abandoned.

[51] Int. Cl.⁶ .................................................. G01N 33/53
[52] U.S. Cl. .................. 435/6; 435/7.21; 435/7.92; 435/7.93; 435/7.94; 435/970; 435/975; 436/501; 436/503; 436/807; 436/809; 422/68.1; 422/69
[58] Field of Search .................. 435/6, 7.21, 7.92, 435/7.93, 7.94, 970, 975; 436/501, 503, 807, 809; 422/68.1, 69; 530/413

[56] References Cited

U.S. PATENT DOCUMENTS

| | | | |
|---|---|---|---|
| 5,262,297 | 11/1993 | Sutton | 435/5 |
| 5,270,164 | 12/1993 | Anderson et al. | 435/6 |

OTHER PUBLICATIONS

Harper et al Molecular Pharmacology 42 pp. 603–612 (1992) "In Vitro Transformation of the Human Ah Receptor and Its Binding to a Dioxin Response Element".

Gasiewicz et al Molecular Pharmacology 40 pp. 607–612 (1991) "α–Napthoflavone Acts as an Antagonist of 2,3,7,8-Tetrachloro–dibenzo–p–dioxin by Forming an Inactive Complex with the Ah Receptor".

Reyes et al Science 256 pp. 1193–1195, (22 May 1992) "Identification of the Ah Receptor Nuclear Translator Protein (Arnt) as a component of the DNA Binding Form of the Ah Receptor".

Poland et al Molecular Pharmacology 39 pp. 20–26 (1991) "characterization of Polyclonal Antibodies to the Ah Recepor Prepared by Immunization with a Synthetic Peptide Hapten".

*Primary Examiner*—Margaret Parr
*Assistant Examiner*—Lora M. Green
*Attorney, Agent, or Firm*—Nixon, Hargrave, Devans & Doyle

[57] ABSTRACT

The present invention is directed to a method of detecting dioxin-like compounds in a test sample. The test sample is contacted with a heteromer formed from a plurality of proteins, one of which is an inactive Ah receptor. If dioxin-like compounds are present in the test sample, they will bind to the Ah receptor causing it to dissociate from the heteromer as a complex containing active Ah receptor bound to a dioxin-like compound ligand. The presence of the complex is then detected. The process of the present invention can be practiced utilizing solid phase capture, competitive, and sandwich immunoassay test kit formats.

25 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:1:

```
Cys  Xaa  Arg  Lys  Arg  Arg  Lys  Pro  Val  Gly  Lys  Thr  Val  Lys  Pro
 1                  5                             10                            15
Ile  Pro  Ala  Glu  Gly  Ile  Lys
                    20
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

GATCTGGCTC TTCTCACGCA ACTCCG        26

( 2 ) INFORMATION FOR SEQ ID NO:3:

( i ) SEQUENCE CHARACTERISTICS:
        ( A ) LENGTH: 26 base pairs
        ( B ) TYPE: nucleic acid (C) STRANDEDNESS: single
(D) TOPOLOGY: unknown (ii) MOLECULE TYPE: DNA (genomic)

(xi) SEQUENCE DESCRIPTION: SEQ ID NO:3:

GATCCGGAGT TGCGTGAGAA GAGCCA    26

(2) INFORMATION FOR SEQ ID NO:4:

(i) SEQUENCE CHARACTERISTICS:
    (A) LENGTH: 32 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:4:

GATCCGGCTC TTCTCACGCA ACTCCGAGCT CA    32

(2) INFORMATION FOR SEQ ID NO:5:

(i) SEQUENCE CHARACTERISTICS:
    (A) LENGTH: 31 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:5:

GATCTGACTC GGAGTTGCGT GAGAAGAGCC G    31

(2) INFORMATION FOR SEQ ID NO:6:

(i) SEQUENCE CHARACTERISTICS:
    (A) LENGTH: 26 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:6:

GATCCGGAGT TGCGTGAGAA GAGCCA    26

(2) INFORMATION FOR SEQ ID NO:7:

(i) SEQUENCE CHARACTERISTICS:
    (A) LENGTH: 26 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:7:

TGGCTCTTCT CACGCAACTC CGGATC    26

(2) INFORMATION FOR SEQ ID NO:8:

(i) SEQUENCE CHARACTERISTICS:
    (A) LENGTH: 7 amino acids
    (B) TYPE: amino acid
    (C) STRANDEDNESS: single
    (D) TOPOLOGY: unknown (ii) MOLECULE TYPE: peptide ( x i ) SEQUENCE DESCRIPTION: SEQ ID NO:8:

Lys Arg Arg Lys Pro Val Gly
1               5

IMMUNOASSAY FOR AH RECEPTOR TRANSFORMED BY DIOXIN-LIKE COMPOUNDS

This is a continuation-in-part of U.S. patent application Ser. No. 795,193, filed Nov. 19, 1991, now abandoned which is a continuation-in-part of U.S. patent application Ser. No. 792,922, filed Nov. 15, 1991, now abandoned.

FIELD OF THE INVENTION

The present invention is directed to the detection of transformed Ah receptor and the consequent indirect detection of dioxin-like compounds by detection of transformed Ah receptor.

BACKGROUND OF THE INVENTION

Introduction

Over the last several decades, dioxins have become the subject of intense scrutiny. This is due to their great toxicity and their assumed widespread presence in the environment. The toxicology of dioxins has been addressed principally through studies of their biological action using animal models and cell culture systems. In addition, the potential threat that dioxins present to human health has been addressed in only a limited manner through epidemiologic studies of populations known to have been exposed to dioxins. The environmental issues have been addressed through the study of the production, release, and degradability of dioxin. Although dioxins have been extensively studied in these ways, their exact mechanism of toxicity in biological systems and their extent of environmental distribution are unknown. This is due in part to the lack of a simplified method of assessing the exposure of biological systems to dioxins and related compounds. The present invention is directed to overcoming this deficiency in the art.

TCDD and Related Chemicals in the Environment

The term dioxin, as commonly used by the news media, is shorthand for 2,3,7,8-tetrachlorodibenzo-p-dioxin ("TCDD"). TCDD is only one member (i.e. congener) of the polychlorinated dibenzo-p-dioxin family, of which there are 75 possible congeners whose structures vary according to the number and location of the chlorine atoms. A source of confusion is that the term "dioxin" is used to indicate either TCDD specifically, or the polychlorinated dibenzodioxin (PCDD) family in general. Biologically, TCDD is the most potent PCDD; most other PCDDs are less active by a factor ranging from ten to thousands. TCDD has been studied most extensively of all the PCDD congeners.

Several aromatic hydrocarbons share biological properties with TCDD, particularly when substituted with chlorine in the lateral positions. The most important of these are the polychlorinated dibenzofurans ("PCDF") and certain members of the polychlorinated biphenyl family ("PCB"). The large number of possible PCDD (75), PCDF (135), and PCB (20) congeners greatly complicates environmental analysis, and complex clean-up procedures are required before such analysis can be undertaken. As used herein, "dioxin-like compounds" includes all members of the above-identified families of compounds and other compounds that induce similar cellular effects, such as azobenzenes and benzopyrenes. TCDD came to scientific and public attention in the early 1970s as a contaminant of the defoliants 2,4,5-trichlorophenoxyacetic acid and 2,4-dichlorophenoxyacetic acid, notably through forest spraying programs in the U.S. and in Viet Nam.

Prior TCDD Detection Techniques

The principle methods for detection of dioxin-like compounds over the past decade have involved the use of physico-chemical analysis. Such procedures generally involve one or more sample clean-up steps to extract an analyte from the original sample, gas chromatography to separate the analyte of interest from admixture with other compounds, detection by mass spectrometry, and identification of the analyte by comparison to known synthetic standards. These procedures are reviewed in R. E. Clement, "Ultratrace Dioxin and Dibenzofuran Analysis: 30 Years of Advances", *Analytical Chemistry*, vol. 63, no. 23 (1991) and *Analytical News* (September/October 1992). Although sensitive, these techniques are not suitable for screening large numbers of samples due to their high cost (i.e., up to $2500 per sample) and the need for the analyses to be carried out at centralized labs by skilled operators. In addition, physico-chemical analysis of dioxin-like compounds is not amenable to the prediction of toxicity of mixtures of dioxin-like compounds or the identification of dioxin-like compounds for which no synthetic standards exist.

Another approach for the detection of dioxin-like compounds has been the use of bioassays in which living cells or animals are dosed with a test sample and then analyzed for the induction of cytochrome P450IA1 activity—a property thought to suggest the presence of dioxin-like compounds.

A number of references disclose cell-line bioassays. In D. E. Tillitt et al., "Characterization of the H4IIE Rat Hepatoma Cell Bioassay as a Tool for Assessing Toxic Potency of Planar Halogenated Hydrocarbons in Environmental Samples," *Environ. Sci. Technol.*, vol. 25, no. 1, pp. 87–92 (1991) utilizes H4IIE rat hepatoma cells to assess the overall toxic potency of various dioxin-like compounds. After such cells were treated with a test sample, they were subjected to spectrofluorometric analysis to detect aryl hydrocarbon hydroxylase and ethoxyresorufin-O-deethylase activity (indicative of cytochrome P450IA1 induction). T. Zacharewski, "Applications of the In Vitro Aryl Hydrocarbon Hydroxylase Induction Assay for determining '2,3,7,8-Tetrachlorodibenzo-p-dioxin Equivalents'; Pyrolyzed Brominated Flame Retardants," *Toxicology*, 51: 177–89 (1986) ("Zacharewski") is generally similar.

Bioassays requiring live animals have also been utilized. In Zacharewski, rats were injected with test samples and killed. Hepatic microsomal enzyme fractions were recovered and subjected to enzymatic analysis to detect aryl hydrocarbon hydroxylase or ethoxyresorufin-O-deethylase induction.

Although bioassays have been used extensively in the literature, they do not have practicable commercial utility. The chief disadvantage of such assays is their need for live cells or animals, making them unsuitable for a commercial test kit format. In addition, the enzymatic detection of P450IA1 is not very sensitive and requires sophisticated instrumentation.

Due to the above-noted problems associated with physico-chemical analysis and bioassays, increasing attention has been focused on in vitro assays for detection of dioxin-like compounds.

In C. A. Bradfield, et al., "A Competitive Binding Assay for 2,3,7,8-Tetrachlorodibenzo-p-Dioxin and Related Ligands of the Ah Receptor,"*Molecular Pharmacology*, 34:682–88 (1988), an ammonium sulfate fraction of liver cytosol from C57BL/6J mice was incubated with a test sample and the radioligand $[I^{125}]$2-iodo-7,8-dibromodibenzo-p-dioxin. Free ligands were then removed by charcoal treatment and bound radioactive ligands were measured with a scintillation counter. This procedure suffers from a number of disadvantages, including the need to obtain a permit for use of radioisotopes and the requirement for equipment to detect and dispose of such radioactive materials. In addition, this assay only measures binding which is not related to toxicity.

In M. Vanderlaan, et al., "Environmental Chemistry—Improvement and Application of an Immunoassay for Screening Environmental Samples for Dioxin Contamination," *Environmental Toxicology and Chemistry*, vol. 7, pp. 859–70 (1988), levels of dioxin-like compounds in test samples were determined with a direct immunoassay having monoclonal antibodies which bind to the dioxin-like compounds themselves. See also M. Vanderlaan, "ES&T Critical Review—Environmental Monitoring by Immunoassay," *Environ. Sci. Technol.*, vol. 22, no. 3, pp. 247–54 (1988). Such assays are not particularly useful, because they do not distinguish between toxic and non-toxic chemicals all of which may be structurally similar.

U.S. Pat. No. 4,904,595 to Gierthy relates to an epithelial cell line and its use in an in vitro bioassay for dioxin-like activity. Upon exposure to dioxin, a morphological change is induced in the subject XBF cell line, cocultured with lethally irradiated 3T3 cells, to a flat cobblestone appearance, as compared with the fusiform high density state in control cultures not treated with dioxin.

U.S. Pat. No. 4,798,807 to Vanderlaan, et al. discloses monoclonal antibodies which react with dioxin-like compounds and a method of using these antibodies in a sensitive immunoassay for such compounds. These antibodies recognize and bind to dioxin-like compounds in a competitive immunoassay.

U.S. Pat. No. 4,238,472 to Albro, et al. discloses a radioimmunoassay method to detect dioxin-like compounds in environmental samples. This method involves combining a sample containing dioxin (emulsified with detergent) with a first antibody which binds to dioxin and radioactive $I^{125}$ labelled dioxin to form an antibody-$I^{125}$-dioxin complex. This causes the labelled and unlabelled dioxin to compete for binding with the antibody. The complex is then reacted with a second antibody to form a precipitate containing dioxin. The radioactivity in the precipitate is assayed, and a curve is utilized to determine the amount of dioxin in the sample Another approach for detection of dioxin-like compounds is suggested by M. M. Stantostefano, et al., "Effects of Ligand Structure on the In vitro Transformation of the Rat Cytosolic Aryl Hydrocarbon Receptor," *Archives of Biochemistry and Biophysics*, vol. 297, no. 1, pp. 73–79 (1992). As illustrated in FIG. 4 of that paper, the formation of a dioxin responsive element and a dioxin responsive element binding protein complex is correlated to the concentration of dioxin-like compounds using gel shift analysis. Although this approach is of scientific interest, it is not a suitable commercial format.

In view of the above-noted deficiencies of prior techniques for detecting dioxin-like compounds, the need remains for technology which will accurately detect toxic dioxin-like compounds in a commercially suitable, inexpensive format.

SUMMARY OF THE INVENTION

The present invention relates to a method of detecting, in a test sample, polychlorinated dibenzodioxins, polychlorinated dibenzofurans, polychlorinated biphenyls, and structural analogues thereof which exhibit biological activity characteristic of such compounds via transformation of the Ah receptor. This method utilizes a heteromer formed from a plurality of proteins, one of which is an Ah receptor in inactive form. A test sample is brought in contact with the heteromer under conditions effective to bind any polychlorinated dibenzodioxins, polychlorinated dibenzofurans, polychlorinated biphenyls and the like in the test sample to the Ah receptor. The binding of such ligands to the Ah receptor causes a complex containing Ah receptor bound to the ligand to dissociate from the heteromer and transform into an active state. The presence of the complex containing transformed Ah receptor bound to the ligand is then detected.

The method of the present invention can be carried out with any one of several immunoassay test kit formats. One suitable format is a solid phase capture immunoassay test kit which includes the heteromer, an antibody with a region capable of binding to the complex and a label to permit detection of the antibody, and a solid support. Also suitable is a competitive immunoassay test kit format which includes the heteromer, a binding substance having a first region capable of binding to a solid support and a second region capable of binding to the complex, an analogue with a region capable of binding to the binding substance and a label to permit detection of the analogue, and a solid support. Another suitable format is a sandwich immunoassay test kit which includes the heteromer, a binding substance having a first region capable of binding to a solid support and a second region capable of binding to the complex, an antibody with a region capable of binding to the complex with a label to permit detection, and a solid support.

The assay can be used directly in the field and does not contain any environmental contaminants other than what may be present in the sample to be measured. Samples can be assayed in the same day, and the results of many air, water, or soil samplings can be reported on-site. Such availability of on-site results allows for immediate evaluation of remediation efforts.

DETAILED DESCRIPTION OF THE DRAWINGS AND INVENTION

Figure 1:
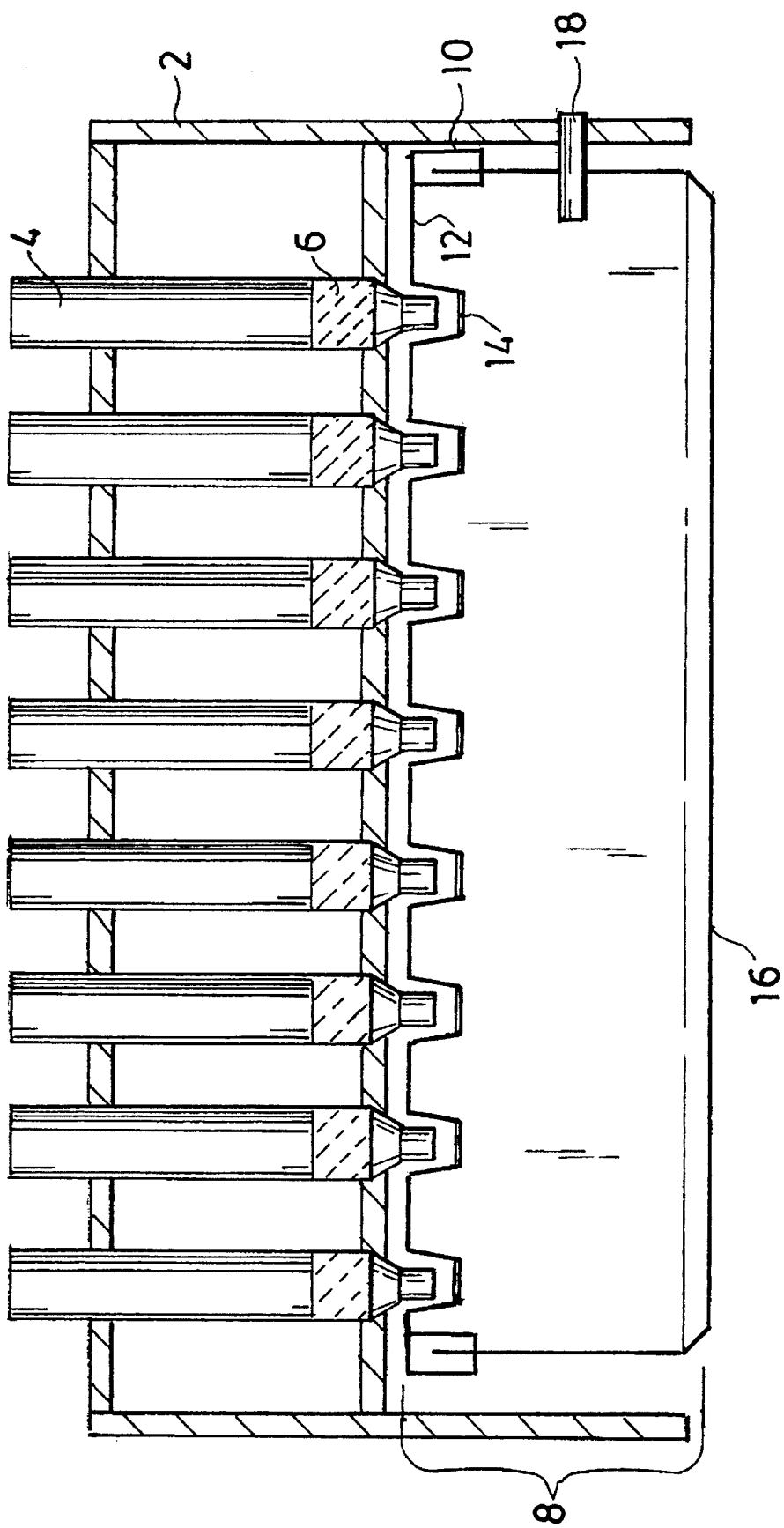
FIG. 1 shows a format for a modified solid phase capture immunoassay test kit.

The present invention relates to a method of detecting, in a test sample, polychlorinated dibenzodioxins, polychlorinated dibenzofurans, polychlorinated biphenyls, and structural analogues thereof which exhibit biological activity characteristic of such compounds. This method utilizes a heteromer formed from a plurality of proteins, one of which is an Ah receptor in inactive form. A test sample is then brought in contact with the heteromer under conditions effective to bind polychlorinated dibenzodioxins, polychlorinated dibenzofurans, polychlorinated biphenyls, and the like, in the test sample, to the Ah receptor. The binding of such ligands to the Ah receptor causes a complex containing active Ah receptor bound to the ligand to dissociate from the heteromer. The presence of the complex containing active Ah receptor bound to the ligand is then detected.

The process by which the dioxin-like compounds bind to the Ah receptor and cause the active Ah receptor bound to the ligand to dissociate is known as transformation. The inactive Ah receptor exists as one of at least three proteins which form a cytosolic high molecular weight heteromer. Although the precise composition and structure of the heteromer is unknown, it is believed that heat shock protein 90 is another one of the constituent proteins. Upon ligand binding to the Ah receptor, the Ah receptor dissociates from the complex and undergoes a conformational change to a heterodimer complex that has increased affinity for cationic exchangers and double stranded DNA. This process of activating the Ah receptor is essentially irreversible. In living cells, activated Ah receptor bound to a ligand enters the nucleus and may bind to the nuclear regulatory sequence of several genes. One such sequence is known as the dioxin responsive element ("DRE"), and interactions between it and the activated Ah receptor are believed to lead to enhanced gene expression. Although the Ah receptor with dioxin-like compound ligands are not themselves toxins, the enhanced gene expression caused by its binding to the dioxin responsive element is believed to be the basis of the toxic response to dioxin-like compounds. The transformation phenomena is discussed in more detail in G. P. Landers et al., "Review Article—The Ah Receptor and the Mechanism of Dioxin Toxicity," *Biochem. J.*, vol. 26, pp. 273–87 (1991) and S. Safe, "Polychlorinated Biphenyls (PCBs), Dibenzo-Dioxins (PCDDs), Dibenzofurans (PCDFs), and Related Compounds: Environmental and Mechanistic Considerations Which Support the Development of Toxic Equivalency Factors (TEFs)," *Toxicology*, vol. 21, pp. 51–87 (1990).

For the present invention, the heteromer containing the Ah receptor can be obtained from any number of sources. Although the heteromer has been identified in several human tissues and cells in culture, including lung, liver, kidney, placenta, B lymphocytes, and thymus, it is preferably obtained from other mammals for ease of availability. The heteromer is present in rodent liver, thymus, lung, kidney, brain, testis, and skeletal muscle cells. A particularly preferred source of the heteromer is a cytosol fraction of mammalian hepatocytes. For example, the heteromer can be obtained by isolating liver cytosol from male Hartley guinea pigs, according to E. C. Henry, et al., "Characterization of Multiple Forms of the Ah receptor: Comparison of Species and Tissues," *Biochem*, 28:6430–40 (1989), and frozen or lyophilized in five milliliter aliquots contained in glass or plastic test tubes.

The process of the present invention is useful for detecting dioxin-like compounds in a variety of test samples. These test samples can be an environmental matrix of air, water, or soil. In addition, the assay can be used to detect dioxin-like compounds in the body fluids (e.g., blood) of humans or animals.

The present detection method is desirably carried out in any conventional test kit format. For example, the immunoassay can be a solid capture, competitive, or sandwich immunoassay.

The solid phase capture immunoassay test kit includes the heteromer, an antibody capable of binding to the complex and having a label to permit detection, and a solid support. The solid support can either be sold as part of the test kit or separate from it. When utilized in the detection method of the present invention, the heteromer is contacted with the test sample. The resulting mixture is contacted with the solid support so that the complex binds to the support. After removal of unbound material, the antibody is contacted with the bound, active Ah receptor. As a result, the label on the antibody can then be detected.

In a particularly preferred form of the present invention, the mixture of heteromer and test sample can be contacted with an affinity matrix so that the complex binds to the affinity matrix. After removal of unbound material, the complex is eluted from the affinity matrix and allowed to contact and adsorb to the solid support. The labelled antibody is then contacted with the adsorbed complex to permit detection. The affinity matrix can also be used to bind to the complex and thereby separate the complex from the remainder of the test sample-heteromer mixture in the sandwich and competitive formats. In each, the complex can be subsequently eluted from the affinity matrix and into absorptive contact with the solid support.

The competitive immunoassay kit includes the heteromer, a binding substance having a first region capable of binding to a solid support and a second region capable of binding to the complex, an analogue with a region capable of binding to the binding substance in the second region and having a label to permit detection of the analogue, and a solid support. When this competitive immunoassay test kit format is utilized in the detection method of the present invention, the binding substance is contacted with the solid support so that the former binds to the latter. The analogue is then contacted with the binding substance under conditions causing the analogue to compete with the complex, formed during contact between the test sample and the heteromer, to be bound to the second region of the binding substance. After such competition, the step of detecting takes place. Here, the presence of the complex is detected indirectly by analyzing for the labeled analogue.

The sandwich immunoassay kit contains a binding substance having a first region capable of binding to a solid support and a second region capable of binding to the complex, the heteromer, an antibody with a region capable of binding to the complex containing active Ah receptor bound to the ligand and having a label to permit detection of the antibody, and a solid support. In use, the binding substance is contacted with the solid support. After the binding substance binds to the solid support and the test sample is contacted with the heteromer, the mixture of test sample and heteromer is placed in contact with the solid support. As a result, the complex binds to the second region of the binding substance. Following removal of the unbound mixture, the labelled antibody is contacted with the complex bound to the solid support. As a result, the label on the antibody can be detected.

The solid support used in any of these immunoassay test kit formats may be any water insoluble, water suspendible solid material conventionally utilized in such kits. Suitable examples are polymeric membranes, plastic or glass beads, test tubes, or microtiter plates. The binding substance in the complex, containing active Ah receptor bound to the ligand, may be bound to the solid carrier by covalent binding or adsorption. When test tubes or microtiter plates are utilized, such bonding takes place at the inner walls of these carriers.

In the competitive and sandwich immunoassay test kits, the kit can be merchandised with the binding substance already bound to the solid support. Such application to the solid support surface is achieved by contacting the binding substance with the solid support and maintaining such contact for sufficient time to permit the first region of the binding substance to bond to the solid support. Typically, such contact takes one to eighteen hours, preferably four hours. The non-adhered binding substance is then separated from the insolublized binding substance (i.e., that which is bound to the solid support) and the solid support is then washed.

In all three immunoassay test kit formats, the test sample and the heteromer are placed in contact with each other and allowed to incubate for sufficient time to permit transformation. Typically, such transformation takes two hours. Such contact desirably is followed by contacting the test sample and heteromer mixture with a solid support. For the solid phase capture assay, the complex binds directly to the solid support, while the complex binds indirectly (i.e., through the binding substance) to the solid support in the competitive assay or sandwich immunoassays. For all three immunoassay test kit formats of the present invention, after allowing sufficient time for incubation, residual test sample and heteromer mixture is separated from the insolublized material bound to the solid support. The insoluble material is then washed.

After the labelled antibody for the solid phase capture or the labelled analogue for the competitive immunoassay test kit are contacted with insolubilized material bound to the solid support, such contact is maintained for sufficient incubation time so that the labelled material bonds indirectly to the solid support. Typically, one hour to eighteen hours, preferably two hours, is sufficient for such binding. The unbound material is then separated from the insolubilized material, and the insolubilized material is then washed.

For the solid phase capture, competitive, and sandwich immunoassay test kit formats, a labelled analogue or antibody (as the case may be) is needed to detect the extent to which that analogue or antibody indirectly bonds to the solid support. Such detection preferably involves a quantitative measurement of the labelled material. For the solid phase capture, the labeled antibody bonds directly to the complex so that the detection procedures directly determine the amount of complex formed. As to the competitive immunoassay test kit, the labelled analogue which is actually detected is insolubilized at sites where the complex is not present. Thus, the amount of complex formed must be determined indirectly from the amount of analogue detected. The label can be a colored, fluorescent, chemiluminescent, radioactive, or enzymatic material conjugated to the antibody or analogue, or a colored, fluorescent, chemiluminescent, radioactive, or enzymatic material conjugated to a secondary binding substance such as an antibody that binds to the binding substance that interacts with the complex.

For the sandwich and solid phase capture immunoassay test kits, an antibody capable of binding to the complex containing active Ah receptor bound to a dioxin-like compound ligand is used. The antibodies can be in polyclonal or monoclonal form.

A particularly preferred procedure for obtaining detection antibodies is to synthesize the following peptide sequence modified from the mouse Ah receptor N-terminus:

Amino-Cys-Nor-Arg-Lys-Arg-Arg-Lys-Pro-Val-Gly-Lys-Thr-Val-Lys-Pro-Ile-Pro-Ala-Glu-Gly-Ile-Lys-carboxyl SEQ. ID. No. 1

Note that Nor is norleucine. The unpurified peptide is coupled to ovalbumin using maleimidobensoyl-N-hydroxysuccinimide ester with a yield of 9 to 22 moles of peptide per mole of ovalbumin. Rabbits are then immunized with 0.5 to 1 mg quantities of the antigen at bi-weekly intervals and bled after 8 weeks and thereafter. Serum is obtained from the blood of the rabbits. To purify the anti-Ah antibody, the peptide (SEQ. ID No. 1) is covalently linked to an iodoacetamide derivatized column through the sulfhydryl group on the terminal cysteine of the peptide. Antibodies to the Ah receptor N-terminus are purified from the serum by affinity chromatography on the above-described column. The preferred label for the antibody is commercially available anti-rabbit IgG alkaline phosphatase conjugate.

For the competitive immunoassay, a labelled analogue, which is capable of binding to the second part of the binding substance is used. Suitable analogues include the above peptide sequence (i.e. SEQ. ID. No. 1) coupled to alkaline phosphatase. Alternatively, the analogue can be an antigen which has the same immunological properties and is immunologically equivalent to the activated Ah receptor. See U.S. Pat. No. Re. 32,696 to Schuurs et al. which is hereby incorporated by reference.

The preferred procedure for synthesizing the labeled analogue is to couple alkaline phosphatase to the peptide sequence (SEQ. ID. No. 1) between the sulfhydryl group on the peptide and a primary amine group on the alkaline phosphatase using sulfosuccinimidyl 4-(N-maleimidomethyl) cyclohexane-1-carboxylate coupling.

Enzymatic labels are well known in the art. Examples of such labels include alkaline phosphatase, horseradish peroxidase, glucose-6-phosphate, β-galactosidase, xanthine oxidase, catalase, urease, glucose oxidase, galactose oxidase, β-glucuronidase, and β-B-glucosidase. Such labels are detected by the conversion of substrates to measurable product colorimetrically, fluorometrically, and spectrophotometrically using devices well known in the art. These instruments generate an optical density value which can be converted to a dioxin-like compound concentration by comparison to a standard curve.

Alternatively, the antibody or analogue can be directly labeled. Suitable colored labels include fluorescent, chemiluminescent and colorimetric. These labels are detected by spectrophotometry or densitometry. These instruments generate an optical density value which can be converted to a dioxin-like compound concentration by comparison to a standard curve.

Suitable fluorescent labels for the antibody or analogue include fluorescein, rhodamine and their derivatives. These labels are detected by fluorimetry. These instruments generate an optical density value which can be converted to a dioxin-like compound concentration by comparison to a standard curve.

Suitable chemiluminescent labels include luminol, isoluminol, acridinium esters, thioesters, sulfonamides, and phenathridinium esters. These labels generate an optical density value which can be converted to a dioxin-like compound concentration by comparison to a standard curve. Such labelling systems produce a long-lived glow of light. This glow can be detected with luminometers, photomultiplier tubes, and solid state detectors.

The competitive and sandwich immunoassays both utilize a binding substance with a first region capable of binding to the solid support and a second region capable of binding to a complex containing active Ah receptor bound to a dioxin-like compound ligand. The binding substance is preferably selected from the group consisting of an antibody, a dioxin responsive element, and a portion of the dioxin responsive element.

Where the binding substance is in the form of an antibody, such antibodies can be polyclonal or monoclonal. The binding substance can be composed of calf thymus DNA adsorbed or covalently coupled to a solid support or specific DNA sequences adsorbed or covalently coupled to a solid support.

It is particularly preferred to utilize the dioxin responsive element or portions thereof to form the binding substance. The DNA sequences for the dioxin responsive element of cells in various species has been the subject of extensive investigation.

In M. S. Dennison et al., "Characterization of the Interaction of Transformed Rat Hepatic Cytosolic Ah Receptor R with a Dioxin Responsive Transcriptional Enhancer," *Arch. of Biochemistry and Biophysics*, vol. 284, pp. 158–66 (1991), the following synthetic nucleotide sequences were used:

5'-GATCTGGCTCTTCTCACGCAACTCCG-3'   SEQ. ID. No. 2

5'-GATCCGGAGTTGCGTGAGAAGAGCCA-3'   SEQ. ID. No. 3

Once synthesized, these sequences can be annealed to form a double stranded DNA sequence.

T. A. Gasiewicz, "Accelerated Communication—alpha-naphthoflavone Acts as an Antagonist of 2,3,7,8-Tetrachlorodibenzo-p-Dioxin by Forming an Inactive Complex with the Ah Receptor, *Molecular Pharmacology,*" 40:607–12 (1991) utilizes the following nucleotide sequences:

5'-GATCCGGCTCTTCTCACGCAACTCCGAGCTCA-3'
SEQ. ID. No. 4

5'-GATCTGACTCGGAGTTGCGTGAGAAGAGCCG-3'
SEQ. ID. No. 5

These sequences can be annealed to form single core recognition sequence for the DNA binding form of the Ah receptor.

It is particularly desirable to utilize a DNA sequence prepared by annealing the following sequences of nucleotides:

5'GATCCGGAGTTGCGTGAGAAGAGCCA-3'   SEQ. ID. No. 6

5'TGGCTCTTCTCACGCAACTCCGGATC-3'   SEQ. ID. No. 7

Both of these sequences are prepared with a DNA synthesizer with the latter being synthesized with a 5 prime amino modifier C6-TFA. This linker provides a primary amine with the 6-carbon spacer at the 5' end. For further chemical modification, these 2 nucleotide sequences are dissolved in 20 mM (3-[N-Morpholino]propanesulfonic acid buffer pH 7.6 plus 1 mM ethylenediaminetetraacetic acid in equimolar amounts, hybridized by heating to 90° C. for five minutes, and cooled to 37° C. overnight. The hybridized dioxin-responsive elements are then covalently coupled to cyanogen-bromide activated sepharose beads.

Other dioxin responsive element nucleotide sequences are disclosed in D. W. Nebert, et. al., "Minireview—Regulation of the Mammalian Cytochrome $P_1$-450(CYP1A1) Gene", *Int. J. Biochem*, vol. 21, no. 3, pp. 243–52 (1989), which is hereby incorporated by reference.

In a particularly preferred form of the solid phase capture immunoassay of the present invention, the apparatus of FIG. 1 is utilized. This device includes holder 2 having a plurality of small polypropylene columns 4. Columns 4 have open ends and are each fitted with a affinity matrix 6 at the bottom thereof.

Also shown in FIG. 1, is solid phase capture unit 8. Solid phase capture unit 8 includes capture member holder 10 formed from e.g., a polyethylene 96-well flat bottom plate 12 with holes in the bottoms of each well. Nitrocellulose discs constituting capture membranes 14 are cemented into these holes. Container 16 with vacuum manifold outlet 18 is designed to fit under capture membrane holder 10.

In use, cytosol with heteromer containing inactive Ah receptor is mixed with a test sample that may contain dioxin-like compounds. After the mixture incubates for a few hours, it is pipetted into each of columns 4 in holder 2. Effluent passing through the columns drains into a waste container (not shown).

After the affinity matrix columns are treated with a mixture of test sample and cytosol, rack 2 with columns 4 are placed over capture membrane holder 8 with the bottom end of each column 4 extending into a well of plate 12, as shown in FIG. 1. Active Ah receptor with dioxin-like compound ligands is then eluted from affinity matrix 6 and binds with capture membrane 14. Excess liquid is drawn away from capture membrane 14 by the vacuum manifold 18. A labelled antibody can then be added to the capture membrane to detect the presence of active Ah receptor with dioxin-like compound ligands.

Again, affinity matrix 6 can be utilized in the sandwich and competitive immunoassay formats of the present invention. In much the same manner as described above for the solid phase capture format, the affinity matrix is contacted with the mixture of test sample and heteromer so that the complex binds to the matrix. The bound complex is then eluted from the matrix and brought in contact with and absorbed on a solid support.

The immunoassays of the present invention have a number of potential uses. One use for this assay would be the one step determination of toxic equivalent factors ("TEFs"). TEFs are a measure of the toxic potential of Ah receptor-dependant toxins and can be used in the hazard and risk assessment of such compounds. The assay could be used to screen for anti-estrogenic drugs used for mammary tumor therapy. The assay could also be used to screen potential natural or synthetic TCDD antagonists which may have potential as anti-promotional agents or in cancer prevention. It could be a rapid screen for dioxin-like toxicity in pharmaceutical and agrichemical products. In basic research, the assay could be used as an endpoint in experiments for studying the cellular events that effect Ah receptor transformation in human cell lines, in order to understand human susceptibility to dioxin-like compounds. The assay could be used to determine exposure status to TCDD and dioxin-like compounds in human or animal tissues and cells, the response of human Ah receptor to TCDD and PCBs, and the levels of Ah receptor in malignant cells.

EXAMPLES

Example 1

Chemicals

All chemicals were purchased from commercial sources and were of the highest purity available.

Antigen Synthesis and Antisera Production

Multiple antigen peptide synthesis (MAPS) was based on a portion of the $NH_2$ terminal of the Ah receptor as reported by Poland et al., *Molecular Pharmacology*, vol. 39, pp.

20–26, (1990). The MAPS antigen consisted of the synthetic peptide H$_2$N-LYS-ARG-ARG-LYS-PRO-VAL-GLY-COOH referred to as SEQ ID No:8 coupled through the carboxyl end of the peptide to a branched lysine septamer. The ratio of peptide to lysine septamer was 8:1. Purity of the antigen was 38% by weight based on amino acid analysis. The antigen was synthesized under contract by TAES laboratory, Entomology Department, Texas A&M University, College Station, Tex. 77843.

Crude antigen was dissolved in phosphate buffered saline at a concentration of 2 mg/ml and 0.5 ml aliquots were mixed with equal volumes of Freund's complete adjuvant (for first immunizations) or Freund's incomplete adjuvant (for subsequent immunizations). Immunizations consisted of 1 ml (380 μg antigen) injected subcutaneously in Flemish Giant/Chinchilla cross rabbits. The immunization schedule was as follows: Injections on day 0, 21, 35, and 49 with blood collection on day 63. Immunizations and blood collection was performed under contract by Cornell Research Animal Resources, Cornell University, Ithaca, N.Y. 14853.

Blood was clotted overnight at 10° C. and the sera isolated by two 20 minute centrifugations at 2900 RPM in an IEC centra-7 centrifuge. One ml aliquots were frozen at −80° C. until further use.

Mouse hepatic cytosol was prepared from female, C57BL/6 mice. Mice were obtained from Jackson Laboratories (Bar Harbor, Me.). Experiments were performed using four to six week old, female mice weighing approximately 16 to 20 g. Mice were fed Prolab RMH 1000 rat, mouse and hamster food (Agway, Cortland, N.Y.) and received tap water ad libitum. All mice were housed three to five per cage and maintained on a photoperiod of 12 hours. Mice were sacrificed and the livers perfused with 1.15% KCl in MENG buffer. Hepatic cytosol fractions were prepared by homogenizing the liver in 3 times the volume of MENG buffer (Poland et al., *Molecular Pharmacology*, vol. 39, 20–26, (1990), which is hereby incorporated by reference). Following a 9000×g centrifugation for 20 minutes, the supernatant (S-9) was centrifuged at 100,000×g for 60 minutes and the resulting cytosol fraction was carefully removed and quickly frozen for storage at −80° C.

Immunoblots

Sodium-dodecyl sulfate polyacrylamide gel electrophoresis was performed according to Laemmli,U.K.,1970, Clevage of structural proteins during the assembly of the head of bacteriophage T4. Nature 227: 680–685). Transfer of resolved proteins onto polyvinylidene difluoride membrane was done according to (Towbin et al.,1979, Electrophoretic transfer of proteins from polyacrylamide gels to nirocellulose sheets: procedures and some applications. Proc. Natl. Acad. Sci. USA 76: 4350–4354). Immunodetection of antigenic proteins on the polyvinylidene difluoride membrane was done according to Poland et al. (1990).

Results

Figure 2:
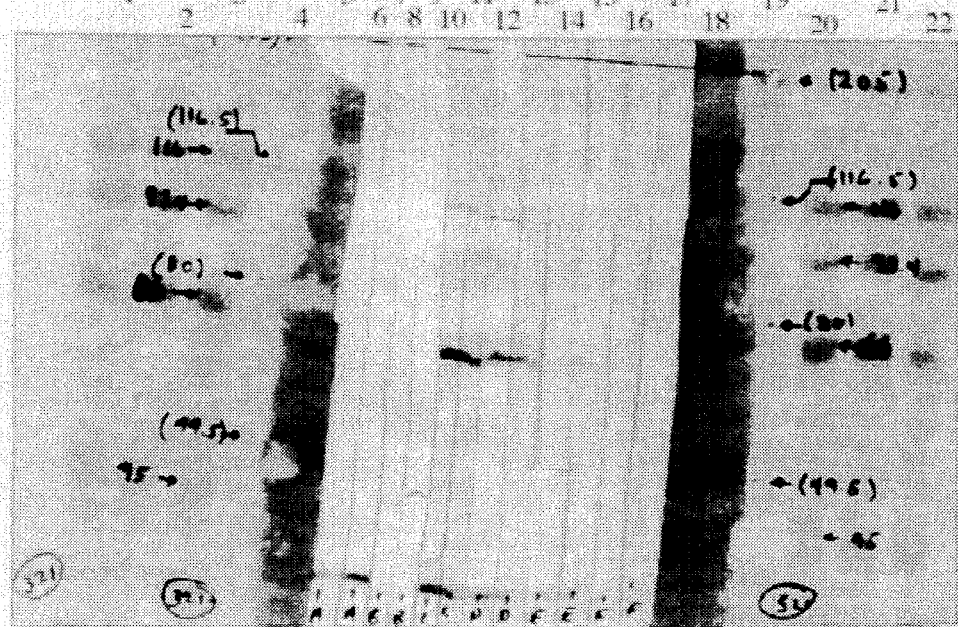
FIG. 2 is a Western Blot gel showing the recognition of mouse liver cytosol proteins by anti-MAPS Antiserum 321. Lanes 5–11 and 13 depict antiserum recognition of 100 kDalton non-ligated form of the Ah receptor at various dilutions of antiserum.

In FIG. 2, lanes 1–3 and 20–22 represent protein standards stained for protein. Standards were (from top to bottom) 116, 97.4, 66, and 45 kDaltons. Lanes 4 and 19 were pre-stained protein standards; these were 205, 116.5, 80, and 49.5 kDaltons, top to bottom, respectively. The total cytosol stained for protein appears in lanes 5 and 18. All other lanes were immunostained with antisera.

The following antisera (with dilution) were used. Anti-MAPS 321-1 (1:11) in lanes 6 and 7, anti-heat shock protein 90 (HSP90, Source) (1:500) in lane 8, anti-MAPS 321-2 (1:11) in lanes 10 and 11, anti-MAPS 321-2 (1:50) in lanes 12 and 13, anti-MAPS 321-2 (1:250) in lanes 14 and 15, and anti-MAPS 321-2 (1:1000) in lanes 16 and 17. The results indicate that the second bleeding rabbit 321 was producing antibodies capable of recognizing the 100 kDalton, nontransformed state of the Ah receptor at a titer of 1:50.

Figure 3:
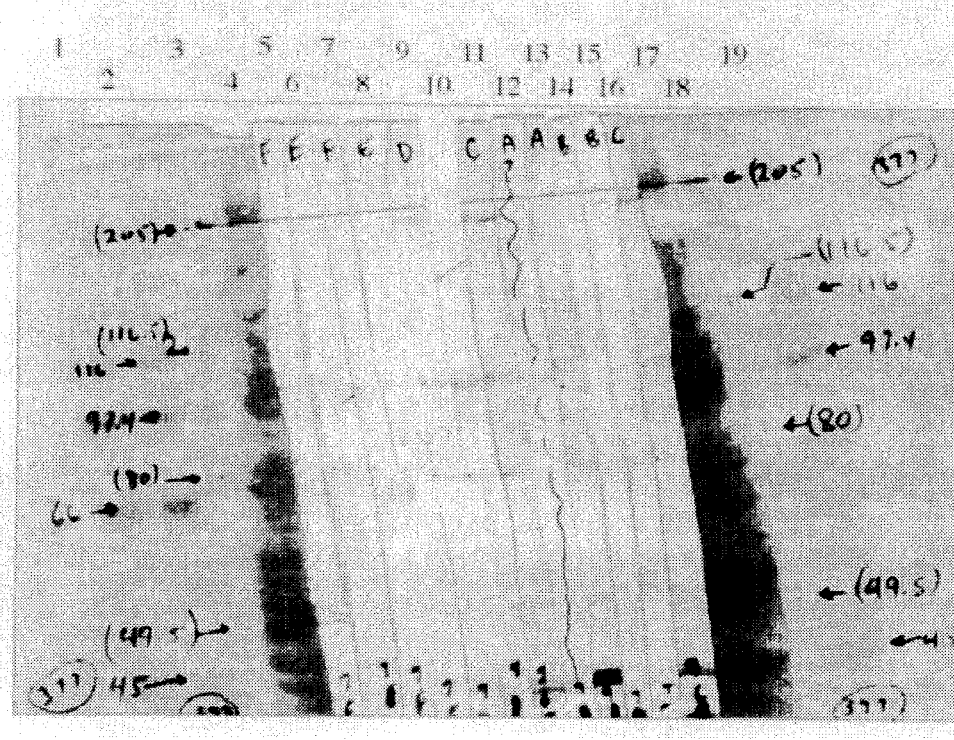
FIG. 3 is a Western Blot gel showing the recognition of mouse liver cytosol proteins by anti-MAPS Antiserum 377. Lanes 1, 2 and 19 are protein standards stained for protein, Lanes 5 and 18 are cytosol stained for protein, and Lanes 12 through 15 depict antisera recognition of 100 kDalton non-ligated form of the receptor.

Lanes 1, 2 and 19 of FIG. 3 represent protein standards stained for protein. Molecular weights represented were 116, 97.4, 66, and 45 kDaltons. The pre-stained standards in lanes 3 and 18 represent molecular weights of 205, 116.5, 80, and 49.5 kDaltons. Cytosol stained for protein was in lanes 4 and 17. All other lanes were immunostained with antisera. The following antisera (with dilution) were used: Anti-MAPS 377-2 (1:250) in lanes 6 and 8, anti-MAPS 377-2 (1:50) in lanes 9 and 10, anti-MAPS 377-2 (1:11) in lanes 11 and 16, anti-MAPS 377-1 (1:11) in lane 13, and anti-HSP90 (1:500) in lanes 14 and 15. These results demonstrate that, at the second bleeding, rabbit 377 was producing antibodies capable of recognizing the 100 kDalton, nontransformed state of the Ah receptor at a titer of 1:250.

Antisera 321-2 and 377-2, prepared against an amino acid sequence of the N-terminus of the Ah receptor, were both capable of recognizing the Ah receptor in which it exists prior to interacting with TCDD or dioxin-like compounds. Such antisera could be used as an assay for dioxin-like compounds by quantitating the amount of nontransformed Ah receptor present in an environmental extract of air, water, or soil. Quantitation could be performed by ELISA techniques, as previously described.

Example 2

This example is set forth with reference to FIG. 1.

Anti-043 polyclonal antiserum was prepared by immunizing rabbits with sequence ID No. 1 coupled to ovalbumin via maleimidobensoyl-N-hydroxysuccinimide ester coupling with a yield of 9 to 22 moles of peptide to carrier. Rabbits were immunized with 0.5 to 1 mg quantities of the antigen at bi-weekly intervals and bled after 8 weeks and thereafter. Serum was obtained from the blood of the rabbits and purified on an affinity column made from peptide sequence ID No. 1 linked to iodoacetamide derivatized agarose beads.

Dioxin-responsive elements (DREs) were made by hybridizing oligonucleotide sequences ID No. 6 (166 nmoles) and ID No. 7 with sequence 7 containing an N-TFA-C6 linker on the 5'end (97 nmoles). These oligonucleotide were dissolved in 20 mM (3-[N-morpholino] propanesulfonic acid buffer pH 7.6 plus 1 mM ethylenediaminetetraacetic acid and hybridized by heating to 90° C. for five minutes, and cooled to 37° C. overnight. The hybridized dioxin-responsive elements were then covalently coupled to cyanogen-bromide activated sepharose beads as follows. Dry beads (1.14 g) were placed in a scintered glass funnel attached to a vacuum aspirator. The beads were swollen by washing sequentially with ice cold 250 ml 1 mM HCl, cold 300 ml deionized water, and cold 40 ml 10 mM potassium phosphate buffer pH 8.0. The beads plus DREs were then incubated 16 hours at room temperature with gentle rocking. The beads were then washed with 200 ml water and 100 ml 1M ethanolamine pH 8, resuspended in 5.6 ml ethanolamine buffer, and incubated 6 hours at room temperature with rocking. The beads were then washed with 100 ml water, 100 ml 10 mM potassium phosphate buffer pH 8.0, 100 ml 1M potassium phosphate pH 8.0, 100 ml 1M KCl, and 100 ml 10 mM Tris(hydroxymethyl)aminomethane-HCl (pH 7.6) containing 0.3M NaCl, 1 mM ethylenediaminetetraacetic acid, and 0.02% sodium azide. The resulting affinity matrix was made into two 2.4 ml bed volume open columns in 10 ml syringe barrels and stored at 4° C.

Male Hartley guinea pigs (300–350 g) were obtained from Charles River. Livers were perfused with ice cold 1.15% KCl in HEDG buffer (25 mM N-[2-hydroxyethyl]piperazine-N'-[2-ethanesulfonic acid], 1.5 mM ethylenediaminetetraacetic acid, 1.0 mM dithiothreitol, pH 7.6) and homogenized on ice in five volumes (wt/vol) HEDG buffer. The livers were homogenized, and the extract centrifuged at 12,500× g for 20 minutes. The supernatant was then re-centrifuged at 100,000×g for 60 min, and the supernatant (hepatic cytosol) was frozen at −80° C.

Cytosol (5 mL) from guinea pigs was treated with 5 µl 10 µM 2,3,7,8-tetrachlorodibenzo-p-dioxin (TCDD) in dimethyl sulfoxide (final concentration=10 nM) or 5 µl dimethyl sulfoxide only and both allowed to incubate for 2 hours at ambient temperature. Cytosol was then incubated with 500 µl charcoal (10%)/dextran (1%) in HEDG buffer for 15 min on ice to remove unbound TCDD. The charcoal/dextran was removed by filtering the cytosol through a 0.45 µm polysulfone filter. The filtered cytosols were then passed through an affinity matrix column, followed by 2×4 ml HEDG, 2×4 ml HEDG plus 350 mM NaCl, and 2×4 ml HEDG plus 600 mM NaCl. The last washes were collected and 800 µg bovine serum albumin in 800 µl water was added to each followed by 8.8 ml 20% ice cold trichloroacetic acid. The proteins were allowed to precipitate on ice for 30 min and centrifuged in a clinical centrifuge for 30 min. The supernatant was discarded and the precipitate was dissolved with 100 µl 1M TRIS pH 8.0, 400 µl water and 500 82 1 2 X sample buffer (5 mM Tris, 0.05% bromphenol blue, 2% mercaptoethanol, 2% sodium dodecyl sulfate, 10% glycerol, pH 6.8). The dissolved proteins were denatured by boiling 5 min and 100 µl each analyzed by sodium dodecyl sulfate polyacrylamide gel electrophoresis (Laemmli, 1970) followed by blotting onto polyvinylidene difluoride according to Towbin et al. (1979). Protein standards were run in adjacent lanes. The lane containing protein standard was stained with 0.1% amido black 10B in 7% acetic acid and destained in 7% acetic acid. The lanes containing the column eluants were incubated in blocker buffer (5% non-fat dry milk in TBST (50 mM TRIS, 150 mM NaCl, 0.02% Tween 20, pH 7.5)). Incubation conditions were 50 ml and 1 hour. The blot was then probed with 40 ml anti-043 antiserum (0.1% in blocker buffer) for one hour. The blot was then washed 3 times, five minutes each, in 100 ml TBST, followed by incubation with 40 ml 0.1% anti-rabbit IgG/alkaline phosphatase conjugate in blocker buffer for one hour, followed by 2 five minute washes with 100 ml TBST, one five minute wash with 100 ml TBST without Tween 20, and a brief wash with alkaline phosphatase development buffer (5.5 g Trizma-base, 0.8 g Trizma-HCl, 2.9 g NaCl, 5.1 g MgCl$_2$-6H$_2$O). The blot was developed with 3.3 mg 5-bromo-4-chloro-3-indolyl-phosphate and 6.6 mg nitroblue tetrazolium in 20 ml alkaline phosphatase development buffer for 5 min, washed several times with water, and dried.

Figure 4:
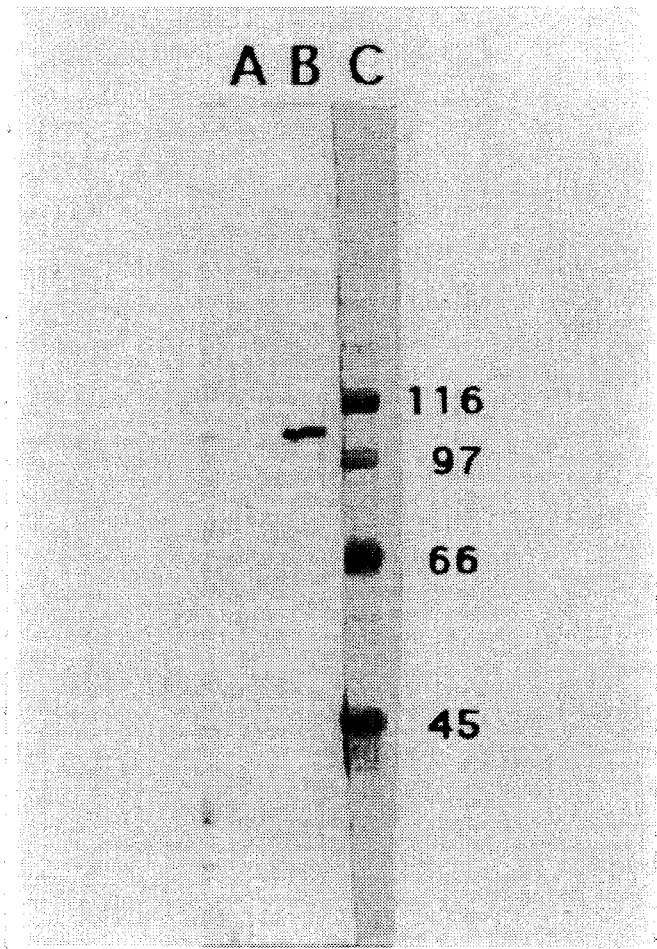
FIG. 4 is a Western Blot gel demonstrating the specific immuno-detection of Ah receptor transformed by TCDD.

In FIG. 4, Lane A was loaded with affinity matrix eluant from solvent treated cytosol. Lane B was loaded with affinity matrix eluant from 10 nM TCDD treated cytosol. Lane C was loaded with molecular mass standards, identified by kD in vertical column.

Results, as shown in FIG. 4, demonstrate that the anti-043 antiserum detects a single protein band in the column eluant. The presence of the protein is TCDD dependent, since it appears in the TCDD treated sample but not the solvent treated sample. The estimated molecular mass (circa 105 kD) is identical to guinea pig Ah receptor. It binds to a dioxin-responsive element as transformed Ah receptor is predicted to do. It is recognized by an antiserum made to a peptide sequence specific and conserved among mammalian Ah receptors. Thus, these results demonstrate that the treatment of cytosol with dioxin-like compounds followed by isolation and immunodetection of transformed Ah receptor can detect the presence of dioxin-like compounds. Furthermore, the immunodetection of a single TCDD-responsive band indicates the protocol is specific to the detection of transformed Ah receptor and can be modified into a simple immunoassay test kit without the need of resolving unwanted immuno-reactive proteins.

Example 3

This example is set forth with reference to FIG. 5. Methodology was identical to that in Example 2 except for the following changes. Aliquots (2 ml each, TCDD treated sample and solvent treated sample) of the 8 ml, 600 mM NaCl eluant, from the affinity matrix were diluted with 0.5 ml methanol. Replicate 0, 50, 100, 200, or 400 µl samples were dot-blotted onto nitrocellulose and the fluid passed through the membrane using a vacuum manifold. The membrane was then probed with anti-043 antiserum and developed as in Example 2. The membrane was then scanned on a Microtek 600ZS scanner at 300 dpi, −18% brightness, 0% contrast. Densitometric measurements were made using Scan Analysis 2.21 software by BioSoft, Cambridge, United Kingdom, on a Macintosh IIsi.

Figure 5A:
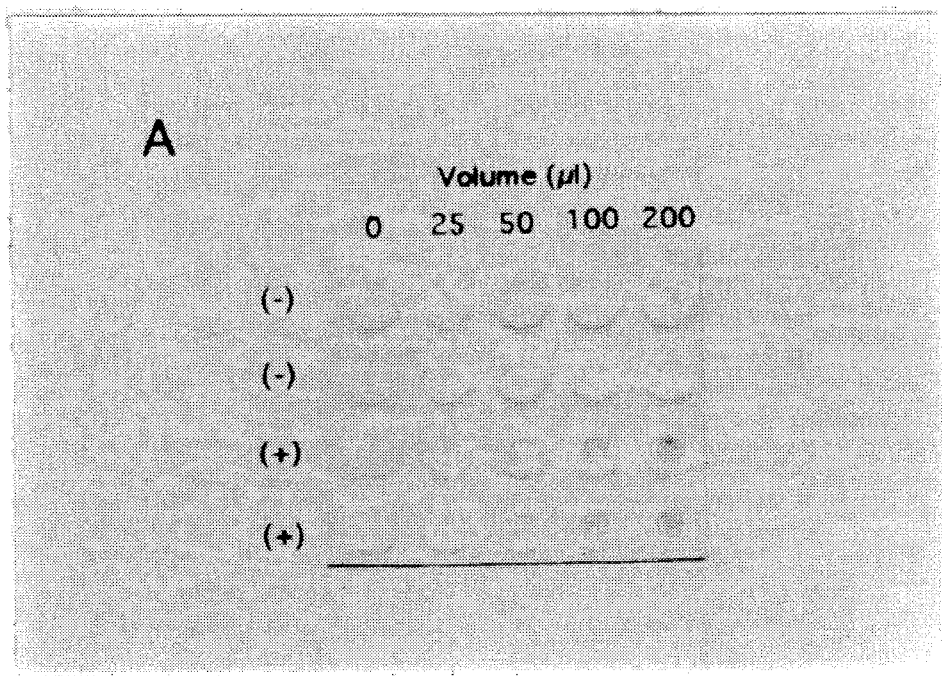
FIG. 5A shows a nitrocellulose sheet dot blot demonstrating the capture and detection of TCDD-transformed Ah receptor onto nitrocellulose.
Figure 5B:
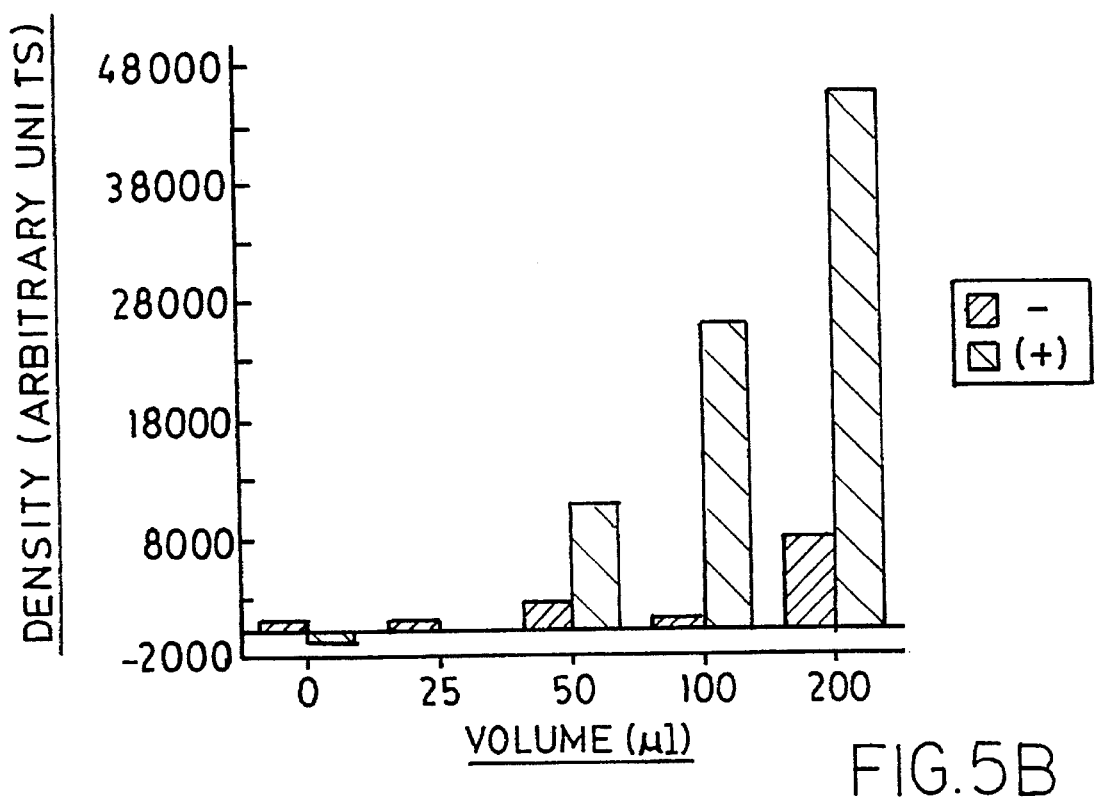
FIG. 5B is a graph of density versus volume of TCDD derived from scanning the dot blot of FIG. 5A.

In FIG. 5, volumes given are equivalent to original cytosol preparation. (−): solvent treated cytosol, (+): 10 nM TCDD treated cytosol. FIG. 5A shows the nitrocellulose sheet with color due to the presence of transformed Ah receptor. FIG. 5B are averaged density data derived from scanning the dot blot in FIG. 5A. Hatched bars: Sovent control. Solid bars: 10 nM TCDD treatment.

Results indicate that nitrocellulose efficiently captures the transformed Ah receptor, with low background. Increasing volumes of TCDD treated sample produced increasing color development which could be seen by the naked eye, while increasing volumes of solvent treated sample showed no or little color development. Good sensitivity and linear capture was seen in the range of 50 to 200 µl sample loadings. These results demonstrate the suitability of the solid-phase capture assay format utilizing nitrocellulose as the solid support and a vacuum manifold to pull the sample through the membrane. In addition, the rapid and easily visualized formation of insoluble permanent color on the membrane suggest this is a suitable format for a semi-quantitative rapid field test which does not require spectrophotometric equipment.

Example 4

This example is set forth with reference to FIG. 6. The methodology was identical to Example 2 except for the following changes. Affinity matrix columns were prepared as described in Example 2 but were formed into multiple 100 µl bed volume columns in 1 ml tuberculin syringe barrels. Cytosol (500 µl) was transformed with variable amounts (0, 0.016, 0.08, 0.4, 2, 10 nM; corresponding to 0, 13, 64, 320, 1600 pg TCDD respectively). After loading the samples onto the mini-columns, they were washed with 2×160 µl HEDG, 2×160 µl HEDG plus 350 mM NaCl, and 2×160 µl HEDG plus 600 mM NaCl. The last wash was collected, and 32 µg bovine serum albumin and 350 µl 20% trichloroacetic acid was added and precipitated proteins isolated and analyzed by SDS-PAGE and blotting as before. Blots were probed as before until the last detection step. At this point, bands in the position of Ah receptor were excised from the blot and placed in test tubes. In addition, identical control strips were excised (lanes with only sample buffer loaded). To each strip, 300 μl of 1 mg/ml para-nitrophenylphosphate in diethanolamine buffer (1 mM $MgCl_2$-$6H_2O$, 50 mM diethanolamine, 0.02% NAN3, pH 9.8) was added and the whole incubated at room temperature for 1 hour. The colored solution(s) were then pipetted into 96 well ELISA plates and the O.D read at 405 nm. Data were subtracted from controls values.

Figure 6:
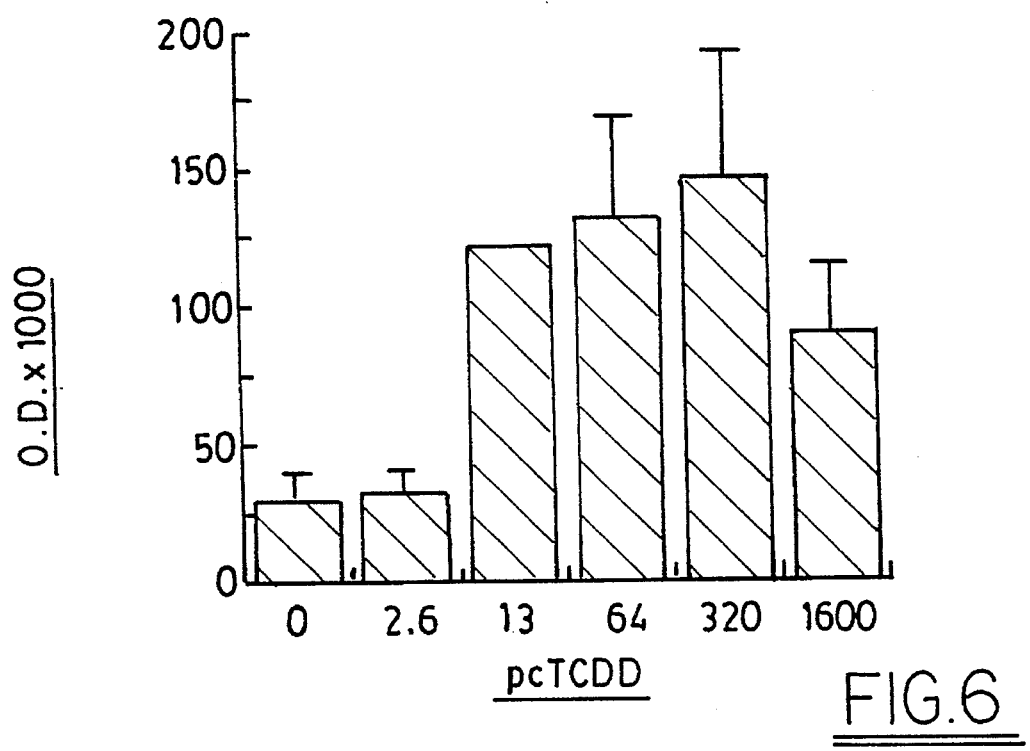
FIG. 6 shows a graph of optical density versus dose of TCDD.

FIG. 6 shows the dose response to TCDD. Error bars represent standard deviations (n=3 for all samples except 13 pg treatment, where n=2)

Results indicated that 1) small volumes of cytosol and small affinity matrix columns could be used in the assay, 2) soluble alkaline phosphatase para-nitrophenylphosphate could be used as a detection format so that a quantitative assay response could be realized using an ELISA reader. In addition, the detection limit of this experiment was on the order of 0.08 nM, or 13 pg, with the response of the assay saturated above that.

Example 5

Methodology was identical to Example 3 except that the volume of cytosol treated per sample was increased from 500 μl to 800 μl, and the dose range of TCDD used was 0, 0.0032, 0.016, 0.08, 0.4 and 2 nM. The resulting data showing optical density at different TCDD concentrations is set forth below in Table 1.

TABLE 1

| nM TCDD | O.D. @ 405 nm × 1000 |
|---------|----------------------|
| 2.0     | 214 ± 52.1*          |
| 0.4     | 156 ± 69.5*          |
| 0.08    | 166 ± 84.1*          |
| 0.016   | 132 ± 45.2*          |
| 0.0032  | 54 ± 25.1            |
| 0       | −53 ± 79.6           |

*significantly different from 0 nM dose using 2-tailed t-test @ p = 0.05, n = 3.

Results show that, similar to Example 3, the response is essentially saturated between 0.08 and 2 nM. However, increasing the amount of cytosol allowed the detection of 0.016 nM or 5 pg TCDD.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of detecting, in a test sample, a ligand selected from the group consisting of polychlorinated dibenzodioxins, polychlorinated dibenzofurans, polychlorinated biphenyls, and structural analogues thereof comprising:

provinding a heteromer from a cytosol fraction of mammalian hepatocytes, wherein the heteromer is formed from a plurality of proteins, in which one of the proteins is an Ah receptor in inactive form;

contacting the test sample with the heteromer under conditions effective to bind said ligand in the test sample to the Ah receptor, causing the heteromer to undergo transformation, resulting in dissociation from the heteromer of a complex containing active Ah receptor bound to said ligand; and detecting the presence of the complex containing active Ah receptor bound to said ligand and thereby detecting the presence of said ligand in the test sample, wherein said detecting comprises:

capturing the complex containing active Ah receptor bound to said ligand on a solid support on which a dioxin responsive element is immobilized;

contacting the complex with a labelled antibody so that the labelled antibody binds to the complex; and detecting the complex containing active Ah receptor bound to said ligand by detecting the labelled antibody.

2. A method according to claim 1, wherein said detecting provides a quantitative measurement of the complex.

3. A method according to claim 1, wherein the test sample is an environmental matrix selected from the group consisting of air, water, and soil.

4. A method according to claim 1, wherein the heteromer is from a cytosol fraction of guinea pig hepatocytes.

5. A sandwich immunoassay test kit for detecting, in a test sample, a ligand selected from the group consisting of polychlorinated dibenzodioxins, polychlorinated dibenzofurans, polychlorinated biphenyls, and structural analogues thereof comprising:

a solid support;

a dioxin responsive element having a first region capable of binding to said solid support and a second region capable of binding to a complex containing active Ah receptor bound to said ligand;

a heteromer from a cytosol fraction of mammalian hepatocytes, wherein said heteromer is formed from a plurality of proteins, one of which proteins is the Ah receptor in inactive form, wherein, upon contact with a test sample containing said ligand, said ligand binds to the Ah receptor, and said heteromer undergoes transformation, causing dissociation from the heteromer of the complex containing active Ah receptor bound to said ligand; and an antibody with a region capable of binding to the complex containing active Ah receptor bound to said ligand, wherein said antibody is provided with a label to permit detection of said antibody.

6. A sandwich immunoassay test kit according to claim 5, wherein said dioxin responsive element is prepared by annealing the following nucleotide sequences:

5'GATCCGGAGTTGCGTGAGAAGAGCCA-3'   SEQ. ID. No. 6

5'TGGCTCTTCTCACGCAACTCCGGATC-3'   SEQ. ID. No. 7

7. A sandwich immunoassay test kit according to claim 5, wherein the label is a colored, fluorescent, chemiluminescent, radioactive, or enzymatic material conjugated to said antibody.

8. A sandwich immunoassay test kit according to claim 5, wherein said dioxin responsive element is immobilized on said solid support.

9. A sandwich immunoassay test kit according to claim 5, wherein the heteromer is from a cytosol fraction of guinea pig hepatocytes.

10. A competitive immunoassay test kit for detecting, in a test sample, a ligand selected from the group consisting of polychlorinated dibenzodioxins, polychlorinated dibenzofurans, polychlorinated biphenyls, and structural analogues thereof comprising:

a solid support;

a dioxin responsive element having a first region capable of binding to said solid support and a second region capable of binding to a complex comprising an active Ah receptor bound to said ligand;

a heteromer from a cytosol fraction of mammalian hepatocytes, wherein said heteromer is formed from a plurality of proteins, one of which proteins is the Ah receptor in inactive form, wherein, upon contact with a test sample containing said ligand, said ligand binds to the Ah receptor, and said heteromer undergoes transformation, causing dissociation from the heteromer of the complex containing active Ah receptor bound to said ligand; and an analogue with a region capable of binding to said second region of the dioxin responsive element, wherein said analogue is provided with a label to permit detection of said analogue.

11. A competitive immunoassay test kit according to claim 10, wherein the label is a colored, fluorescent, chemiluminescent, radioactive, or enzymatic material conjugated to said antibody.

12. A competitive immunoassay test kit according to claim 10, wherein said dioxin responsive element is immobilized on said solid support.

13. A competitive immunoassay test kit according to claim 10, wherein said dioxin responsive element is prepared by annealing the following nucleotide sequences:

5'GATCCGGAGTTGCGTGAGAAGAGCCA-3'   SEQ. ID. No. 6

5'TGGCTCTTCTCACGCAACTCCGGATC-3'   SEQ. ID. No. 7.

14. A competitive immunoassay test kit according to claim 10, wherein the heteromer is from a cytosol fraction of guinea pig hepatocytes.

15. A solid phase capture immunoassay test kit for detecting, in a test sample, a ligand selected from the group consisting of polychlorinated dibenzodioxins, polychlorinated dibenzofurans, polychlorinated biphenyls, and structural analogues thereof comprising:

a dioxin responsive element affinity layer;

a solid support;

a heteromer from a cytosol fraction of mammalian hepatocytes, wherein said heteromer is formed from a plurality of proteins, one of which proteins is the Ah receptor in inactive form, wherein, upon contact with a test sample containing said ligand, said ligand binds to the Ah receptor, and said heteromer undergoes transformation, causing dissociation from the heteromer of a complex containing active Ah receptor bound to said ligand, wherein the complex is capable of binding to said affinity layer and to said solid support; and an antibody with a region capable of binding to the complex, wherein said antibody is provided with a label to permit detection of said antibody.

16. A solid phase capture immunoassay test kit according to claim 15, wherein the label is a colored, fluorescent, chemiluminescent, radioactive, or enzymatic material conjugated to said antibody.

17. A solid phase capture immunoassay test kit according to claim 15 further comprising:

a plate with a plurality of wells each having said solid support at the well bottom, wherein said solid support is a permeable membrane.

18. A solid phase capture immunoassay test kit according to claim 17 further comprising:

a plurality of affinity columns with open ends and a dioxin responsive element affinity layer within each column between the ends, wherein the columns are spaced so that one end can be received within one well of said plate, whereby material eluted from the affinity layer will pass into the well.

19. A solid phase capture immunoassay test kit according to claim 15, wherein the heteromer is from a cytosol fraction of guinea pig hepatocytes.

20. A method of detecting, in a test sample, a ligand selected from the group consisting of polychlorinated dibenzodioxins, polychlorinated dibenzofurans, polychlorinated biphenyls, and structural analogues thereof comprising:

providing a dioxin responsive element affinity layer;

providing a solid support;

providing a heteromer from a cytosol fraction of mammalian hepatocytes, wherein the heteromer is formed from a plurality of proteins with one of the proteins being an Ah receptor in inactive form;

contacting the test sample with the heteromer under conditions effective to bind said ligand in the test sample to the Ah receptor to cause the heteromer to undergo transformation, resulting in dissociation from the heteromer of a complex containing active Ah receptor bound to said ligand;

contacting the complex with said dioxin responsive element affinity layer, whereby the complex binds to the dioxin responsive element;

eluting the complex from said dioxin responsive element affinity layer;

contacting the complex with said solid support, whereby the complex binds to said solid support;

contacting an antibody with the complex bound to said solid support, wherein the antibody has a region capable of binding to the complex and is provided with a label to permit detection of said antibody; and detecting the label to detect the presence of said ligand in the test sample.

21. A method according to claim 20, wherein the heteromer is from a cytosol fraction of guinea pig hepatocytes.

22. A method of detecting, in a test sample, a ligand selected from the group consisting of polychlorinated dibenzodioxins, polychlorinated dibenzofurans, polychlorinated biphenyls, and structural analogues thereof comprising:

providing a solid support;

providing a heteromer from a cytosol fraction of mammalian hepatocytes, wherein the heteromer is formed from a plurality of proteins with one of the proteins being an Ah receptor in inactive form;

contacting the test sample with the heteromer under conditions effective to bind said ligand in the test sample to the Ah receptor, causing the heteromer to undergo transformation, resulting in dissociation from the heteromer of a complex containing active Ah receptor bound to said ligand;

contacting a dioxin responsive element with the solid support, whereby a first region of the dioxin responsive element binds to the solid support;

contacting the complex with the dioxin responsive element bound to said solid support under conditions causing the complex to bind to the second region of the dioxin responsive element;

contacting an analogue with the dioxin responsive element bound to the solid support under conditions allowing the analogue to compete with the complex for binding to said second region of the dioxin responsive element, wherein the analogue is provided with a label to permit detection of the analogue;

detecting the label to indirectly detect the presence of said ligand in the test sample.

23. A method according to claim 22, wherein the heteromer is from a cytosol fraction of guinea pig hepatocytes.

24. A method of detecting, in a test sample, a ligand selected from the group consisting of polychlorinated dibenzodioxins, polychlorinated dibenzofurans, polychlorinated biphenyls, and structural analogues thereof comprising:

providing a solid support;

providing a heteromer from a cytosol fraction of mammalian hepatocytes, wherein the heteromer is formed from a plurality of proteins with one of the proteins being an Ah receptor in inactive form;

contacting the test sample with the heteromer under conditions effective to bind said ligand in the test sample to the Ah receptor, causing the heteromer to undergo transformation, resulting in dissociation from the heteromer of a complex containing active Ah receptor bound to said ligand;

contacting a dioxin responsive element with the solid support, whereby a first region of the dioxin responsive element binds to the solid support;

contacting the complex with the dioxin responsive element bound to said solid support under conditions causing the complex containing active Ah receptor bound to the ligand to bind to a second region of the dioxin responsive element;

contacting an antibody with the complex bound to the second region of the dioxin responsive element, wherein the antibody is capable of binding to the complex containing active Ah receptor bound to said ligand and the antibody has a label to permit detection of said antibody; and detecting the label to detect the presence of said ligand in the test sample.

25. A method according to claim 24, wherein the heteromer is from a cytosol function of guinea pig hepatocytes.

* * * * *